United States Patent
Lauer

(10) Patent No.: US 10,596,308 B2
(45) Date of Patent: Mar. 24, 2020

(54) BLOOD TREATMENT CASSETTE HAVING A DENTED FILM VALVE AND A BLOOD TREATMENT APPARATUS

(71) Applicant: FRESENIUS MEDICAL CARE DEUTSCHLAND GMBH, Bad Homburg (DE)

(72) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 289 days.

(21) Appl. No.: 15/126,261

(22) PCT Filed: Mar. 13, 2015

(86) PCT No.: PCT/EP2015/055320
§ 371 (c)(1),
(2) Date: Sep. 14, 2016

(87) PCT Pub. No.: WO2015/136083
PCT Pub. Date: Sep. 17, 2015

(65) Prior Publication Data
US 2017/0189596 A1    Jul. 6, 2017

(30) Foreign Application Priority Data
Mar. 14, 2014    (DE) .................. 10 2014 103 506

(51) Int. Cl.
*A61M 1/16* (2006.01)
*A61M 39/24* (2006.01)
*A61M 1/14* (2006.01)

(52) U.S. Cl.
CPC ............ *A61M 1/1621* (2014.02); *A61M 1/14* (2013.01); *A61M 39/24* (2013.01);
(Continued)

(58) Field of Classification Search
CPC .... A61M 1/169; A61M 1/1621; A61M 39/24; A61M 2205/3331; A61M 2205/3584;
(Continued)

(56) References Cited

U.S. PATENT DOCUMENTS 6,542,761 B1    4/2003    Jahn et al.
6,645,166 B2    11/2003    Scheunert et al.
(Continued)

FOREIGN PATENT DOCUMENTS

DE    19837667    3/2000
DE    10034711    2/2002
(Continued)

OTHER PUBLICATIONS

International Search Report from PCT/EP2015/055320, dated May 29, 2015.
(Continued)

*Primary Examiner* — Ariana Zimbouski
(74) *Attorney, Agent, or Firm* — Fish & Richardson P.C.

(57) ABSTRACT

The present invention relates to a blood treatment cassette having a cassette body, embodied as a hard part, and a film, wherein the film is connected with the hard part and covers the hard part at least partially, wherein the hard part comprises at least one valve seat or valve section or one valve base of a valve, wherein the valve is embodied to take, in addition to a first, open position of the valve in which the valve base and the section of the film positioned above it do not touch each other, a second, closed position of the valve when applying force on the section of the film and wherein the valve base, in its longitudinal extension, comprises or is a non-straight section. The present invention also relates to a blood treatment apparatus connected with a blood treatment cassette.

8 Claims, 10 Drawing Sheets

(52) U.S. Cl.
CPC . *A61M 2039/246* (2013.01); *A61M 2205/123* (2013.01); *A61M 2205/128* (2013.01); *A61M 2205/3331* (2013.01); *A61M 2205/3584* (2013.01)

(58) Field of Classification Search
CPC ...... A61M 2039/246; A61M 2205/128; A61M 2205/122
See application file for complete search history.

(56) References Cited

U.S. PATENT DOCUMENTS

| | | | |
|---|---|---|---|
| 6,752,172 | B2 | 6/2004 | Lauer |
| 6,821,432 | B2 | 11/2004 | Metzner |
| 6,905,479 | B1 * | 6/2005 | Bouchard ........... F04B 43/0081 604/131 |
| 7,044,432 | B2 | 5/2006 | Beden et al. |
| 7,503,915 | B2 | 3/2009 | Beden et al. |
| 7,648,627 | B2 | 1/2010 | Beden et al. |
| 7,988,686 | B2 | 8/2011 | Beden et al. |
| 8,721,883 | B2 | 5/2014 | Lauer |
| 2002/0062109 | A1 | 5/2002 | Lauer |
| 2003/0100882 | A1 | 5/2003 | Beden et al. |
| 2003/0217961 | A1 * | 11/2003 | Hopping ................. A61M 1/28 210/258 |
| 2003/0218623 | A1 | 11/2003 | Krensky et al. |
| 2006/0079826 | A1 | 4/2006 | Beden et al. |
| 2007/0077068 | A1 | 4/2007 | Mazed |
| 2008/0077068 | A1 * | 3/2008 | Orr ........................... F04B 7/02 604/6.11 |
| 2010/0133153 | A1 | 6/2010 | Beden et al. |
| 2010/0269702 | A1 | 10/2010 | Brueckner et al. |
| 2012/0080437 | A1 | 4/2012 | Guenther et al. |
| 2013/0331774 | A1 | 12/2013 | Farrell et al. |

FOREIGN PATENT DOCUMENTS

| | | |
|---|---|---|
| DE | 10039196 | 2/2002 |
| DE | 10042324 | 2/2002 |
| DE | 10053441 | 5/2002 |
| DE | 102009012632 | 9/2010 |
| JP | 2005-527303 | 9/2005 |
| JP | 2012-524563 | 10/2012 |
| WO | WO 02/25146 | 3/2002 |
| WO | 2010-121819 A1 | 10/2010 |
| WO | WO 2012087798 * | 6/2012 |
| WO | 2012-175435 A1 | 12/2012 |

OTHER PUBLICATIONS

International Preliminary Report on Patentability in Application No. PCT/EP2015/055320, dated Sep. 14, 2016, 8 pages.

* cited by examiner

BLOOD TREATMENT CASSETTE HAVING A DENTED FILM VALVE AND A BLOOD TREATMENT APPARATUS

CROSS REFERENCE TO RELATED APPLICATIONS

The present application is the national stage entry of International Patent Application No. PCT/EP2015/055320, filed on Mar. 13, 2015, and claims priority to Application No. DE 10 2014 103 506.2, filed in the Federal Republic of Germany on Mar. 14, 2014.

FIELD OF INVENTION

The present invention relates to a blood treatment cassette having a cassette body embodied as a hard part and a film, wherein the film is connected with the hard part and covers the hard part at least partially and a blood treatment apparatus connected or provided, configured or suitable to be connected with the blood cassette.

BACKGROUND

Single-use systems are being increasingly realized in the medical or laboratory technology as compact medical functional devices such as cassette systems or blood treatment cassettes in which liquids and gases, in particular medical fluids and blood, are conducted in passages and chambers. If they are provided for a single use, one speaks of disposable cassettes or single-use cassettes.

In most cases, these are hard-part film cassettes. The hard part regularly consists of an injection molding material such as PE, PP, PA, ABS, PMMA, PC or PVC. In it, for example, hose connections, connectors, chambers, channels and alignment devices are embodied. The chambers and channels are usually designed as semi-open, fluid-conducting structures. A film made of material compatible to the hard part (suitable for welding on or gluing to the hard part) seals the semi-open structures and completes them to fully adequate chambers and channels. The film may only be, for example, welded on or glued to the blood treatment cassette at an outer closed or peripheral edge. There also are designs where the boundaries of the chambers and channels, the so-called channel edge bars, are welded on or glued to the film in strip form or over a larger area. In this manner, blood treatment cassettes which already provide a defined fluid conduction prior to being equipped in a treatment machine and after being removed are produced.

Certain areas of the hard part and the film are often deliberately not welded on or glued to each other. These areas may be used as film valves between different fluid-conducting areas. For this purpose, the blood treatment cassette is inserted in the blood treatment apparatus between a door and an actuator-sensor-unit of the blood treatment apparatus, and subsequently by closing the door, the latter is brought into a so-called grouting or pressing position in which the film is grouted or pressed against the hard part, and the blood treatment cassette with the film is coupled in a spatially defined manner to the actuator-sensor-mat of the actuator-sensor-unit. Actuators integrated into the actuator-sensor-mat and actuator-sensor-plate (or unit) may be able to exercise movements through or over the film, by which, for example, pump or valve functions may be realized. Properties of fluids which flow through the blood treatment cassette may be measured by means of at least one sensor optionally provided on the actuator-sensor-plate.

Production or processing problems may however, occur, particularly with blood treatment cassettes in which the films and film valves are welded in such a way that they are flush with the passage edge along the latter.

SUMMARY

One object of the present invention is to provide a further blood treatment cassette. Furthermore, a blood treatment apparatus is to be provided for the use of the blood treatment cassette.

The present invention therefore provides a blood treatment cassette with a cassette body, designed as hard part, and a film. The film is connected to the hard part, e.g., through welding or gluing, and the hard part is at least partially covered by the film against the outside such that channels and chambers or parts thereof, commonly formed by the hard part and the film, are provided. Furthermore, the hard part comprises at least one valve seat or section of a valve, herein also denoted as a valve base of the valve.

The valve is designed or embodied to take a first position and a second position, or valve position, which is different from the first one. Thereby the first position is a position in which the valve is open, in particular for the gas sterilization of sections of the hard part. In the first position, the valve base and a section of the film, which during the use of the treatment cassette is or will be positioned above the valve base, do not touch each other. The valve is configured and provided in a way that it moves or transitions into the second, closed position in case a force is applied, in particular a force directed towards the valve base and acting on the section of the film on top of the valve base. In the second position, the valve base and the section of the film touch each other, for example directly or indirectly. In the second position, the valve is closed.

In addition, the valve base comprises or is in its longitudinal extension a non-straight section.

Further, a blood treatment apparatus according to the present invention is provided, which is connected with a blood treatment cassette or intended, configured or suitable for the connection herewith. It comprises further an actuator-sensor-plate. The actuator-sensor-plate comprises at least one actuator which comprises at least two, preferably more than three, part-actuators. These are arranged in such a way that they exert force—preferably completely or essentially—independently of each other on the section of the film of the valve.

In all of the following embodiments, the use of the expressions "may be" or "may have" etc., is to be understood synonymously with "preferably is" or "preferably has", respectively, and so on, and is intended to illustrate exemplary embodiments according to the present invention.

Whenever a numerical word is mentioned herein, the skilled person understands this as an indication of a numerical lower limit. Provided it does not lead to any contradiction discernible for the skilled person, the skilled person in these cases implicitly understands for example "one" always as "at least one". This understanding is also encompassed by the present invention as well as the interpretation that a numeric word, for example, "one" can alternatively be meant as "exactly one", wherever this is technically possible in the view of the skilled person. Both are encompassed by the present invention and apply to all used numerical words herein.

The spatial information provided herein, such as "top", "bottom", etc. refers to the representations shown in the here enclosed figures provided herein.

Exemplary embodiments according to the present invention may comprise one or more of the following features in any arbitrary combination.

In some particular exemplary embodiments according to the present invention, the valve is designed to be transferrable or to be transferred from the first position into the second position by means of pressure applied on the valve by an actuator of a blood treatment apparatus, for the operation of which the blood treatment cassette is connected with the blood treatment apparatus as intended or designated.

In certain exemplary embodiments according to the present invention, the valve is designed as a film valve or a phantom valve.

The film valves described herein are also referred to as phantom valves in connection with the present invention, as, in a closed state with respect to the concerned channels, they do not constitute any change of the flow area compared to channel points or chambers without film valves. They are not noted or seen or perceived with regard to the flow area like a phantom.

In some particular exemplary embodiments according to the present invention, the non-straight section, referred to herein also as dented section or dent, is not straight because it has different distances to the film plane or to a plane positioned above the film or to the main extension plane of the film or of the blood treatment cassette (for example, initially increasing and then decreasing distance).

The non-straight section may be concave to the film, provided however the latter be even or flat.

In certain exemplary embodiments according to the present invention, the non-straight section is not straight because its distance to the film plane or to the plane, above the film, or to a main extension plane of the film or of the blood treatment cassette is not constant.

In some particular exemplary embodiments according to the present invention, the non-straight section, referred to herein also as the dented section or dent, is not straight because it is formed as shown in FIG. 5.

In some exemplary embodiments according to the present invention, the dent depth of the valve base corresponds to 1 to 3 times of the thickness of the film. Further, the valve base may be reset behind the adjacent channel edge bars by about 1 to 3 times of the thickness of the film towards the interior of the blood treatment cassette.

In some particular exemplary embodiment according to the present invention, the valve base and/or the non-straight section are/is embodied concave or convex (particularly concave to a film plane or main extension plane of the film or of the blood treatment cassette).

In certain exemplary embodiments according to the present invention, the dent depth increases and decreases steadily.

In certain exemplary embodiments according to the present invention, the valve does not comprise both (or not at the same time) an inlet for the main flow and an inlet, distinguishable therefrom, for a secondary flow.

In some exemplary embodiments according to the present invention, the actuator-sensor-plate comprises an actuator-sensor-mat facing the blood treatment cassette. The actuator-sensor-mat comprises a section which is thinner than the adjacent sections and which faces the valve base of the blood treatment cassette.

Some or all embodiments according to the present invention may comprise one or more of the above or below mentioned advantages.

A technical solution is thus proposed by the present invention which allows, in a technically simple manner, a reliable closing of the valve also by given tolerances.

A further advantage is the possible tolerance balance or tolerance compensation according to the present invention which is possible due to the springy positioning of the spacer, however, also due to the multiple-part or laminated design of the actuator for the closing of the film valve. The actuator of the blood treatment apparatus according to the present invention serves as tolerance-balance devices or tolerance-compensation devices for dented, i.e., not straight film-sealing seat-bars, by which an installation tolerance balance or tolerance compensation and a form tolerance balance or tolerance compensation in the direction alongside the sealing seat-bar is ensured for example via independently movable lamellae.

By means of the actuator-sensor-unit, the tolerance-balance devices or tolerance-compensation devices may hereby advantageously maintain the sealing effect of flat or dented film valves and are robust against dimensional tolerances of the blood treatment cassette, the blood treatment device or the alignment between the blood treatment cassette and the blood treatment apparatus. Moreover, it seems that a flow throughout dented film valves may take place more reliably by or with a dented valve base than by a flat one. In any case, the technical effort required for achieving the desired sealing may be less by using dented valves.

A further advantage of dented valves or film valves may be that, with regard to film valves having a flat valve base, at given maximum allowable expansion of the film—against the flat initial state of the film—a greater flow cross section, which may assume double as much, may be achieved when opening the valve with the same overall width of the valve. This is based on the achievable dent depth which is achievable, without damaging the film, with the valve having a dented valve seat and which may be bigger than with flat valve seats.

An allowable maximum expansion may therefore be, for example, 10 to 15%, preferably 12%, of the film length over the extension of the valve base or over the width or length of the cassette.

The present invention shall be exemplarily explained in the following by way of the accompanying drawings, in which identical reference numerals designate same or similar elements.

DETAILED DESCRIPTION

The standard arrows in the figures indicate the direction of the blood stream. The block arrows indicate the respective direction of the substituate stream.

Figure 1:
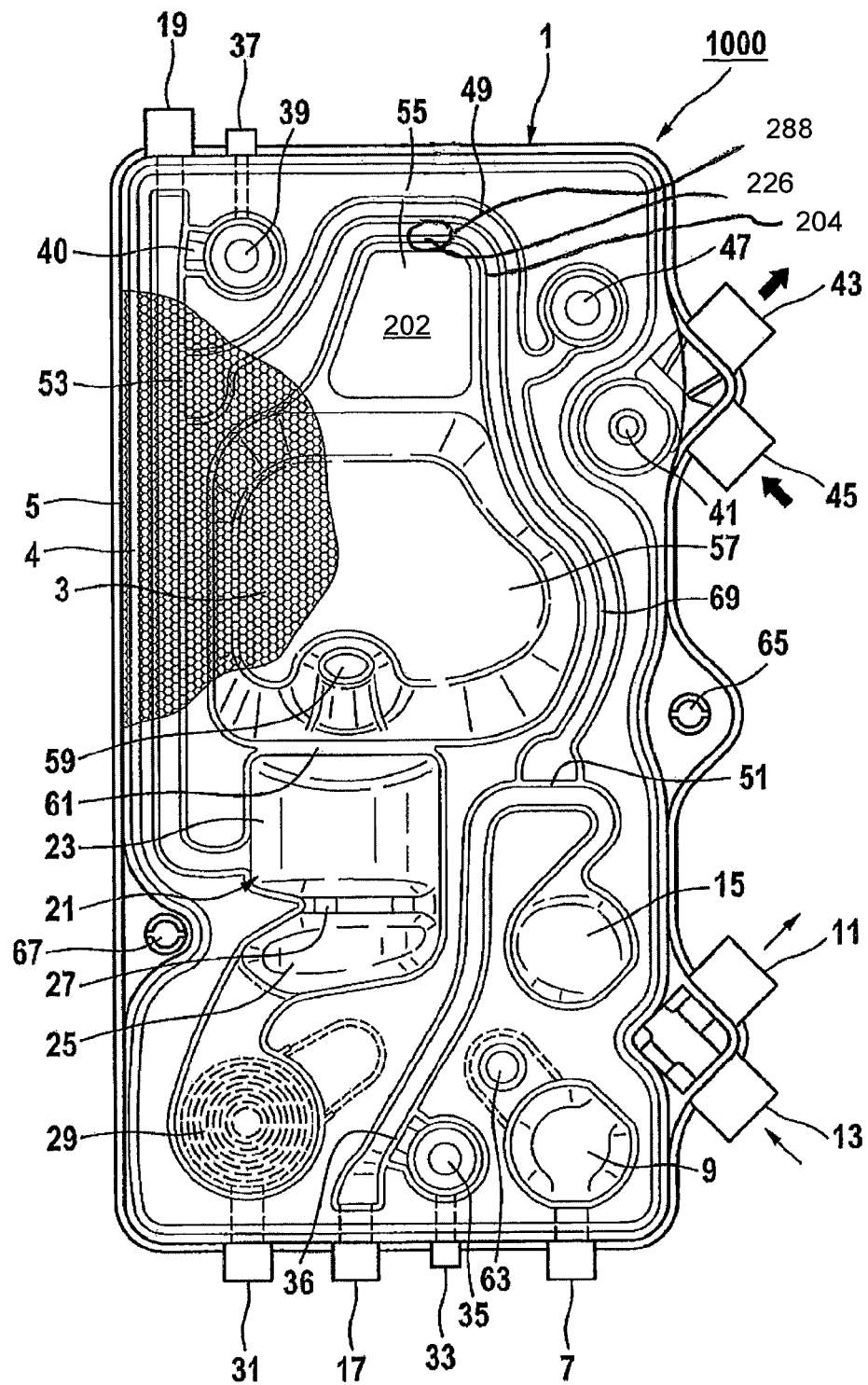
FIG. 1 shows a lateral view of a blood treatment cassette according to the present invention provided in accordance with a preferred embodiment, having a cover means on its front side.

FIG. 1 shows a lateral view of a blood treatment cassette 1000 according to the present invention which is provided with a cover device at the surface one looks upon in FIG. 1.

In the following, the blood treatment cassette 1000 according to the present invention is also referred to as cassette 1000 in short.

The cassette 1000 comprises a hard part 1. As it is exemplarily shown in FIG. 1, the hard part 1 comprises chambers, channels and valves. As it is furthermore exemplarily shown in FIG. 1, the chambers, channels and valves are integrated into the hard part 1 or are at least partly formed by the hard part 1.

The cassette 1000 of FIG. 1 is provided at its front side with a cover means, here, for example, a film 3. The cover means may be welded in a flat manner, i.e., planarly, onto the hard part 1.

An embodiment involving a three-dimensional configuration of the welding and sealing contour is also provided in accordance with the present invention.

The cover means may close the chambers and/or channels of the hard part 1 of the cassette 1000, namely, against a side of the cover means facing away from the hard part 1 and/or against the atmosphere.

As seen in FIG. 1, the film 3 rests on the hard part 1 of the cassette 1000 at a closed sealing bar 4. The film 3 is welded on the hard part 1 of the cassette 1000 at a closed weld 5.

The closed sealing bar 4 may alternatively be realized in an exposed manner.

The film 3 may be connected to the hard part 1 of the cassette 1000 at additional local welds (not shown). These may also be closed or peripheral, i.e., closed in the sense of an enclosing limitation similar to a ring, and/or dot-shaped.

The film 3 may locally be connected, e.g., welded, to the hard part 1 of the cassette 1000 in the form of dots or a line, in particular at the edge zones of the liquid-conducting channels.

The film 3 may be connected to the hard part 1 of the cassette 1000 by laser welding. If so, it is advantageous if heat is locally applied while using a light-absorbing component. The light-absorbing component may be part of the material of the film and/or of the hard part, or a layer disposed between film and hard part or above the film. The layer may be a film layer.

The cassette 1000 may at least be coupled with a blood treatment apparatus (not shown in FIG. 1) at its front side shown in FIG. 1. An exemplary technique for suitable coupling of a cassette 1000 to a coupling surface of a blood treatment apparatus is described in the patent applications DE 10 2009 012 633.3 having the title "Vorrichtung zum Verbinden einer externen Funktionseinrichtung mit einer Anordnung, Anordnung aufweisend eine solche Vorrichtung and Verfahren zum Verbinden" [Device for connecting an external functional means to an arrangement, arrangement including a like apparatus, and connecting method] as filed with the German Patent and Trademark Office on Mar. 10, 2009, and DE 10 2009 012 632.5 having the title "Abdichtungseinrichtung zum Abdichten eines Volumens einer medizinischen Behandlungsanordnung gegen ein weiteres Volumen sowie Anordnung and Verfahren" [Sealing means for sealing a volume of a medical treatment arrangement against another volume, as well as arrangement and method] also filed with the German Patent and Trademark Office on Mar. 10, 2009, the respective disclosures of which are herewith fully incorporated by way of reference.

The cassette 1000 may be coupled with a coupling surface of the blood treatment apparatus by the plane of the film 3 or through the intermediary of the latter. The coupling area may preferably be executed three-dimensionally.

The coupling surface of the blood treatment apparatus may be inclined to the rear, for instance at an upper portion thereof shown in FIG. 1, by 8 degrees against a vertical line extending from top to bottom in FIG. 1 (in the direction extending from the observer into the plane of drawing in FIG. 1).

The cassette 1000 comprises an arterial patient connection 7.

The cassette 1000 comprises an arterial pressure measurement chamber 9. The latter may include corresponding sensors. The sensors may transmit signals, preferably through the intermediary of cables or cabling. The sensors may, however, also be provided to transmit signals in a wireless manner.

The cassette 1000 comprises a connector 11 for the exit of blood from the cassette 1000 as well as a connector 13 for the entry of blood into the cassette 1000.

The two connectors 11 and 13 are adapted to be connected to a pump tube segment or pump tube set of a blood pump.

The cassette 1000 further comprises a chamber 15 including a pressure measurement site for pressure measurement in the extracorporeal blood circuit upstream from the dialyzer ("pre-filter") or downstream from the pump ("post-pump"), respectively.

At the chamber 15 the pressure in the extracorporeal circuit upstream from the dialyzer may be measured across the film 3 or via the film 3.

The cassette 1000 comprises an arterial filter conduit 17 as well as a venous filter conduit 19.

The interior of the cassette 1000 comprises a venous blood chamber 21. The venous blood chamber 21 is subdivided into an upper space 23 and a lower space 25.

The upper space 23 of the venous blood chamber 21 may admit a laterally tangential inflow of blood. Here, blood may flow in laterally through the inlet (on the left side in FIG. 1) into the upper space 23 and spread out tangentially to the walls of the upper space 23. A laterally tangential inflow of blood may create a zone with a substantially or completely stable rotational flow of blood in the upper space 23 of the venous blood chamber 21.

The lower space 25 of the venous blood chamber 21 may represent a calming zone for the blood stream. Such a calming zone may possibly have substantially no rotational flow or no rotational flow of the blood therein at all.

The venous blood chamber 21 is subdivided into the upper space 23 and the lower space 25 by a cross-sectional restriction 27 of the hard part 1 of the cassette 1000. The cross-sectional restriction 27 reduces the cross-section of the venous blood chamber 21 in its width and depth so as to result in a shoot or rapid, whereby a fluid having traversed the cross-sectional restriction 27 will flow with slower flow velocity through the venous blood chamber 21 of the cassette 1000. The upper space 23 and the lower space 25 are in fluid communication.

By means of such a construction, i.e., a subdivision of the venous blood chamber 21 into a zone with substantially or completely stable rotational flow of the blood and a calming zone for the blood stream, it is advantageously possible to achieve an efficient separation of air from the blood or fluid.

Walls of the upper space 23 and of the lower space 25 of the venous blood chamber 21 may suitably be adapted to an inclination from the vertical position of the upper portion of the cassette 1000 in FIG. 1, for example an inclination to the rear by 8 degrees (into the plane of the drawing) of the upper part of the cassette 1000 shown in FIG. 1. They may suitably have a rounded shape such that they advantageously represent a flow-optimized contact surface for fluids passing through the venous blood chamber 21.

The cassette 1000 comprises a clot trap 29.

The clot trap is preferably a clot trap as disclosed in the patent application DE 10 2009 024 495.6 having the title "Gerinnselfänger, externe Funktionseinrichtung, Blutkreislauf sowie Behandlungsvorrichtung" [Clot trap, external functional means, blood circuit and treatment apparatus] to the applicant of the present invention that was filed with the German Patent and Trademark Office on Jun. 10, 2009. The relevant disclosure thereof is herewith fully incorporated by way of reference.

At the clot trap 29, it is possible to measure the pressure in the extracorporeal blood circuit through the film 3 or across the film 3, i.e., in particular after passage through the dialyzer or downstream of the dialyzer.

The cassette 1000 comprises a venous patient connection 31.

The cassette 1000 comprises an arterial heparin addition site 33. Here, it should be noted that the heparin addition site 33 (just like a venous heparin addition site 37) may also be suited and intended for adding other pharmacologically effective agents than heparin, which are only in a preferred manner anti-coagulants or combinations of active agents. This should also be noted whenever heparin is mentioned previously or in the following in any kind of context.

The cassette 1000 comprises a check valve 35 of the arterial heparin addition site 33.

Exemplary check valves for the use as check valve 35 of the arterial heparin addition site 33 and also as further check valves of the cassette 1000 are disclosed in the patent application to the applicant of the present invention DE 10 2009 024 469.7 having the title "Ventilvorrichtung, Ventileinsatz, externe Funktionseinrichtung, Behandlungsvorrichtung sowie Verfahren" [Valve device, valve insert, external functional means, treatment apparatus, and method] as filed with the German Patent and Trademark Office on Jun. 10, 2009, the relevant disclosure of which is herewith fully incorporated by way of reference.

The cassette 1000 comprises an arterial heparin addition valve 36. By means of the arterial heparin addition valve 36 the addition of heparin into the arterial filter conduit 17 may be controlled or regulated.

The arterial heparin addition valve 36 may be configured as a so-called phantom valve.

The expression "phantom valve" as used herein designates an element having an actor surface (in the present case, for example, an actor membrane) that may be reached by means of an actor that may adopt the function of a valve.

The actor membrane can be made to move, dilate or curve etc. in one direction by applying a force on it, e.g., a pressing force. As a result of its movement or dilatation, the actor membrane may come into contact with an element such as a sealing device, e.g., a bar, or move away from the latter. The actor membrane may thus, for example, effect or enhance or terminate or reduce a sealing effect.

When the force acting on the actor membrane is ceased to apply or is released, the latter may return, for example, to a basic position, e.g., a non-bent condition.

A phantom valve for use as an arterial heparin addition valve 36 as well as further phantom valves of the cassette 1000 may be configured with or from a bar portion of a channel at the hard part 1 of the cassette 1000 and a portion of the film 3 contacting or facing the bar portion.

Phantom valves may be operated through actors of the blood treatment apparatus.

In order to close a phantom valve, the portion of the film 3 may be pressed onto the bar portion. In order to open the phantom valve, the portion of the film 3 may again be raised or removed from the bar portion.

Further examples and/or embodiments for phantom valves may be found in the patent application DE 10 2009 012 632.5 having the title "Abdichtungseinrichtung zum Abdichten eines Volumens einer medizinischen Behandlungsanordnung gegen ein weiteres Volumen sowie Anordnung and Verfahren" [Sealing device for sealing a volume of a medical treatment arrangement against another volume, as well as arrangement and method], as filed with the German Patent and Trademark Office on Mar. 10, 2009 by the present applicant besides the patent application (DE 100 53 441 A1) and the patent application (DE 102 24 750 A1). The relevant disclosures thereof are herewith fully incorporated by way of reference.

The cassette 1000 comprises a venous heparin addition site 37. The venous heparin addition site 37 may be configured as a Luer-connector.

The cassette 1000 comprises a check valve 39 of the venous heparin addition site 37.

The cassette 1000 comprises a venous heparin addition valve 40. With the aid of the venous heparin addition valve 40 the addition of heparin into the venous filter conduit 19 may be controlled or regulated.

The cassette 1000 comprises a substituate addition site 41 or a substituate connector, respectively The substituate addition site 41 may be a connection means as it is described in the patent application DE 10 2009 024 575.8 to the present applicant having the title "Verbindungseinrichtung and Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] as filed with the German Patent and Trademark Office on Jun. 10, 2009 by the present applicant. The relevant disclosure thereof is herewith fully incorporated by way of reference.

The substituate addition site 41 may be provided with a touch-protection element (not shown). The substituate addition site 41 may be provided with a drip-protection element (not shown). The drip-protection element may be realized through an integrated closure sleeve. The drip-protection element may prevent residues of substituate and/or blood from dripping out when the cassette 1000 is released and subsequently removed from the blood treatment apparatus.

The drip-protection element may be designed to be removable. It may be configured as a hood or lid.

The substitute addition site 41 or some other portion of the cassette 1000 may moreover provide a tamper protection, as a result of which the user recognizes effortlessly, or at one glance, whether the cassette 1000 has already been used. This tamper protection may be realized by means of the touch-protection element, the closure sleeve, or some other structure. Preferably, the corresponding structure may recognizably change its position inside or relative to the cassette 1000. Preferably it may change its shape.

Moreover, the substitute addition site 41 or some other portion of the cassette 1000 may provide a protection against reuse. In a preferred manner, the cassette 1000 is made unusable by means of a closure sleeve—preferably in an irreversible manner—with respect to an attempted reuse. If the cassette 1000 should nevertheless be used again, sensors of the blood treatment apparatus do not measure the signal characteristics that would be measured during use of a new cassette. This may be due to the fact that liquid cannot enter into the cassette 1000 or into the substitute addition site 41, or at least not in a sufficient or usual quantity. The control unit of the blood treatment apparatus may recognize this. A warning may be triggered.

As a tamper protection or a protection against reuse, it is preferably possible to use a tamper protection or protection against reuse as disclosed by the applicant of the present invention in the patent application DE 10 2009 024 575.8 having the title "Verbindungseinrichtung and Verfahren zum Verbinden wenigstens zweier fluidführender medizintechnischer Systeme, sowie medizintechnische Vorrichtung" [Connection means and method for connecting at least two fluid-conducting medical-technical systems, as well as a medical-technical apparatus] that was filed with the German Patent and Trademark Office on Jun. 10, 2009. The relevant disclosure thereof is herewith fully incorporated by way of reference.

The cassette comprises a connector 43 for the exit of substitute from the cassette 1000 as well as a connector 45 for the entry of substitute into the cassette 1000.

The connectors 43 and 45 are adapted to be connected to a pump tube segment or a pump tube set of a substitute pump.

The cassette 1000 comprises a check valve 47 for the addition of substitute.

Substitute may be introduced into a substitute conduit 49 by operating the check valve 47.

The cassette 1000 comprises a pre-dilution addition valve 51. The pre-dilution addition valve 51 may be configured as a phantom valve.

The cassette 1000 comprises a post-dilution addition valve 53. The post-dilution addition valve 53 may be configured as a phantom valve.

The cassette 1000 comprises a single-needle sterile membrane 55.

The cassette 1000 comprises a single-needle chamber 57. In FIG. 1, the single-needle chamber 57 is disposed above the venous blood chamber 21.

Inside the single-needle chamber 57 a blood surge redirection element 59 is arranged. The blood surge redirection element 59 may serve for decelerating a blood surge and/or extinguishing its impulse.

A connection to an inside of the single-needle chamber 57 may be provided by means of connection means as disclosed by the applicant of the present invention in the patent application DE 10 2009 024 467.0 having the title "Einrichtung sowie externe Funktionseinrichtung and Behandlungsvorrichtung zum Behandeln von medizinischen Fluiden" [Device and external functional means and treatment apparatus for the treatment of medical fluids] that was filed with the German Patent and Trademark Office on Jun. 10, 2009. The relevant disclosure thereof is herewith fully incorporated by way of reference.

The cassette 1000 comprises a single-needle blood valve 61. The single-needle blood valve 61 may be configured as a phantom valve.

The cassette 1000 comprises an evacuation site 63. The evacuation site 63 may serve for vacuum coupling of the cassette 1000 to the blood treatment apparatus as is described, for example, in the patent application DE 10 2007 042 964 A1 having the title "Vorrichtung and Verfahren zur Behandlung einer medizinischen Flüssigkeit" [Apparatus and method for treating a medical liquid] that was filed with the German Patent and Trademark Office on Sep. 10, 2007. The relevant disclosure thereof is herewith fully incorporated by way of reference.

The cassette 1000 comprises a primary alignment center 65. The primary alignment center 65 may advantageously serve for aligning and/or latching of the cassette 1000 on the blood treatment apparatus.

The cassette 1000 comprises a secondary alignment site 67. The secondary alignment site 67 may serve for aligning and/or latching of the cassette 1000 on the blood treatment apparatus.

The cassette 1000 is filled with gas (e.g., sterile air) prior to beginning priming. During priming of the extracorporeal blood circuit this gas filling has to be displaced. Insofar, a blood treatment cassette generally represents a particular challenge as there are both rising and falling conduits and moreover chambers in which no "air nests" must remain. For this purpose, the present cassette 1000 is provided with special construction features:

The chamber 15 for measuring the arterial pressure is constructed such that the entire air may rise into a pump tube segment (e.g., into the pump tube segment 90). Advantageously, there are no dead spaces present. Air rising by itself from the arterial pressure measurement chamber into the pump tube segment of the blood pump is forcibly conveyed through the pump tube segment from the engagement range of the blood pump (e.g., by the rollers of a roller pump). As soon as the pump ceases to exert an influence (for example due to disengaging the rollers), the air rises by itself into the cassette 1000 in the conveying direction.

The venous recirculation conduit (or a venous portion 93 of the extracorporeal blood circuit) is a downward conduit. Starting from a particular herein prevailing volume flow (e.g., 200 ml/min in the case of the cassette 1000 shown in FIG. 1), air bubbles in the blood are "entrained" even against gravitational acceleration or gravitation. This effect is made use of in the downward conduits. The conduit cross-sections of the downward conduits are designed with such a small size that a forcible conveyance of the air bubbles even against gravitational acceleration is successful due to the flow velocity.

In the venous blood chamber 21 large cross-sections are provided, such that air bubbles may reliably rise there against the main direction of flow due to the slower or lower flow velocities present in this location.

Further constructive features of the cassette 1000 are as follows:

The phantom valves 40, 51 and 53 are arranged such that blood (which has a higher density than water or substitute, etc.) can hardly penetrate "upward" or "sideways" into opened phantom valves while the cassette 1000 is operated with blood, for the latter descends as compared to the lighter water. Such an advantageous arrangement is achieved with the aid of the phantom valves 40, 51, and 53. The valve 36, on the other hand, does not imply such a requirement, i.e., the arrangement is not crucial there.

For the same reason, the conduit passage (stub passage) below the check valve 47 for adding substitute is constructed or arranged in a rising manner. In the event of a malfunction of the pre- and/or post-dilution valves 51 and 53 and a resulting bypass flow of blood, blood cannot rise into the substitute conduit 49 anymore. The blood will rather flow past the opening of the corresponding stub conduit.

The inclination of the cassette 1000 preferably is from 5 degrees to 11 degrees, in a particularly preferred manner it assumes the 8 degrees already mentioned above.

Reference numeral 288 denotes a phantom valve which allows in the first position a flow in the chamber 202 or prevents it in a second position. In its simplest embodiment encompassed by the present invention, a phantom valve is a film valve through which a fluid path, between hard part 1 and the section of the film disposed above it, is prevented through temporary pressing of the film 2 on a valve base, like a bar or other sections of the hard part 1, and reopened after release of the pressing force.

The reference numerals 202, 204 and 226 are explained in the description of FIGS. 4 to 12.

Figure 2:
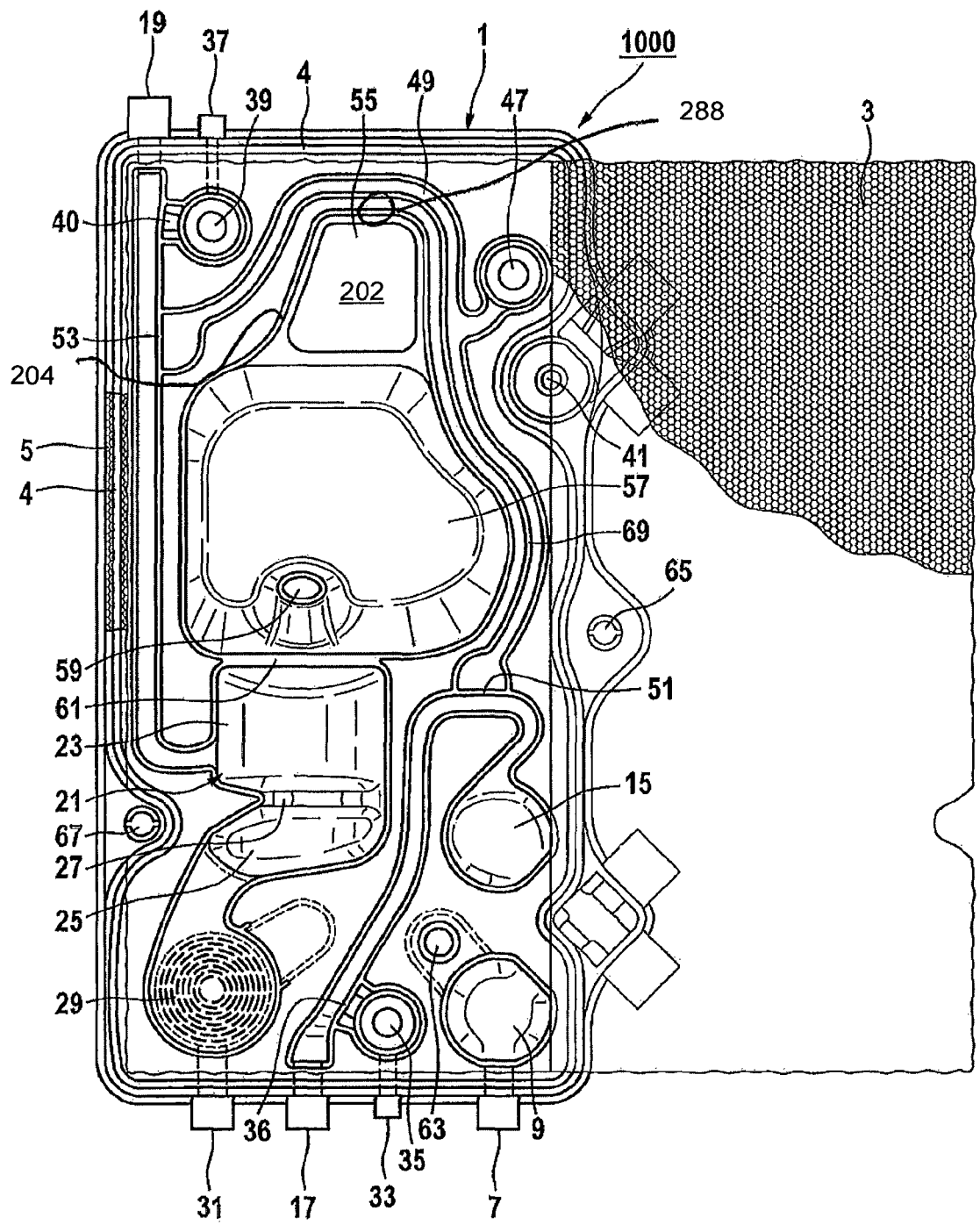
FIG. 2 shows the external functional device of FIG. 1 with the cover means swung-open following destructive cutting.

FIG. 2 shows the cassette 1000 of FIG. 1, wherein the film 3 is recognized to be cut open destructively at the left-hand margin of the cassette 1000 as well as at the top and bottom and swung open to the right for better illustration.

As is shown in FIG. 2, the film 3 comprises a surface texture.

FIG. 2 shows the elements inside the cassette 1000 which are visible in more detail after having cut open the film 3.

Here, it is clearly seen that the cassette 1000 comprises a sealing bar 69. The sealing bar 69 may be employed, for example, for realizing the pre-dilution addition valve 51.

Figure 3:
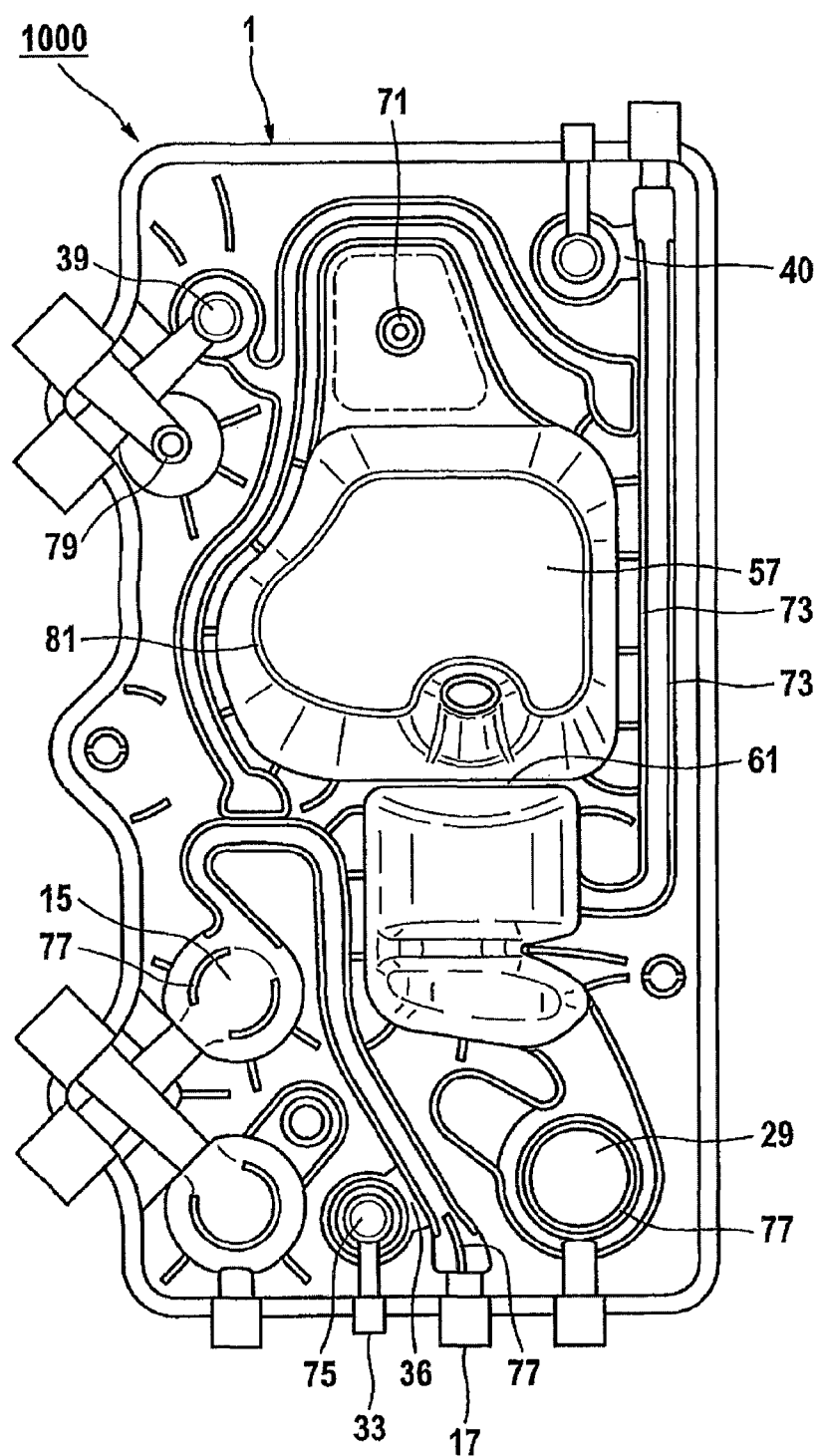
FIG. 3 shows the blood treatment cassette of FIG. 1 and FIG. 2 from its rear side.

FIG. 3 shows the cassette 1000 from its rear side. When the cassette 1000 is coupled with the blood treatment apparatus, an observer opening a door of the blood treatment apparatus for removing the cassette 1000 will look upon this rear side.

The cassette 1000 comprises a single-needle air connector 71. It may be provided to arrange a support grid (not shown) of the single-needle sterile membrane 55 at the single-needle air connector 71 on the apparatus side and/or on the blood side.

The cassette 1000 comprises several support bars. The support bars have different heights relative, e.g., to the plane of the film 3. The support bars are projected in the side of the cassette 1000 facing the observer in FIG. 3, i.e., out of the plane of drawing of FIG. 3.

The cassette 1000 comprises support bars 73 having a height of 5 mm, support bars 75 having a height of 8 mm, support bars 77 having a height of 13 mm, support bars 79 having a height of 24 mm, and support bars 81 having a height of 31 mm. These and other numeric values should, of course, be understood as mere examples.

The support bars may serve to support the cassette, in the state of being coupled to a blood treatment apparatus, against a lid of a reception means of the blood treatment apparatus for receiving the cassette. Exemplary embodiments of such a coupling of the cassette to the blood treatment apparatus are given in the patent application DE 10 2009 012 633.3 having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] as filed with the German Patent and Trademark Office on Mar. 10, 2009, the relevant disclosure of which is herewith fully incorporated by way of reference.

In FIG. 3 the cassette 1000 is shown as it will be viewed by the user/observer after its coupling to the machine interface. The inclination of the cassette 1000 relative to the machine is realized with a "rearward inclination", so that the upper edge is located at a further distance from the user/observer than the lower edge.

The upwardly-facing surfaces of the venous blood chamber 21 and of the single-needle chamber 57 accordingly comprise such an inclination that air bubbles may still reliably rise on the inside despite the inclination of the cassette 1000. As an alternative, a cassette design which does not provide any inclination of the cassette is, of course, also possible.

The following figures show sections of a cassette 1000 according to the present invention which may by all features be in accordance with the cassette 1000 of FIGS. 1 to 3, as long as it does not deviate therefrom in the following described embodiments. In any case, the cassette 1000 of the following figures according to the present invention may comprise features of the cassette 1000 shown in FIG. 1 to FIG. 3 as long as the respective features combinations is not realized by the skilled person to be technically impossible.

Figure 4:
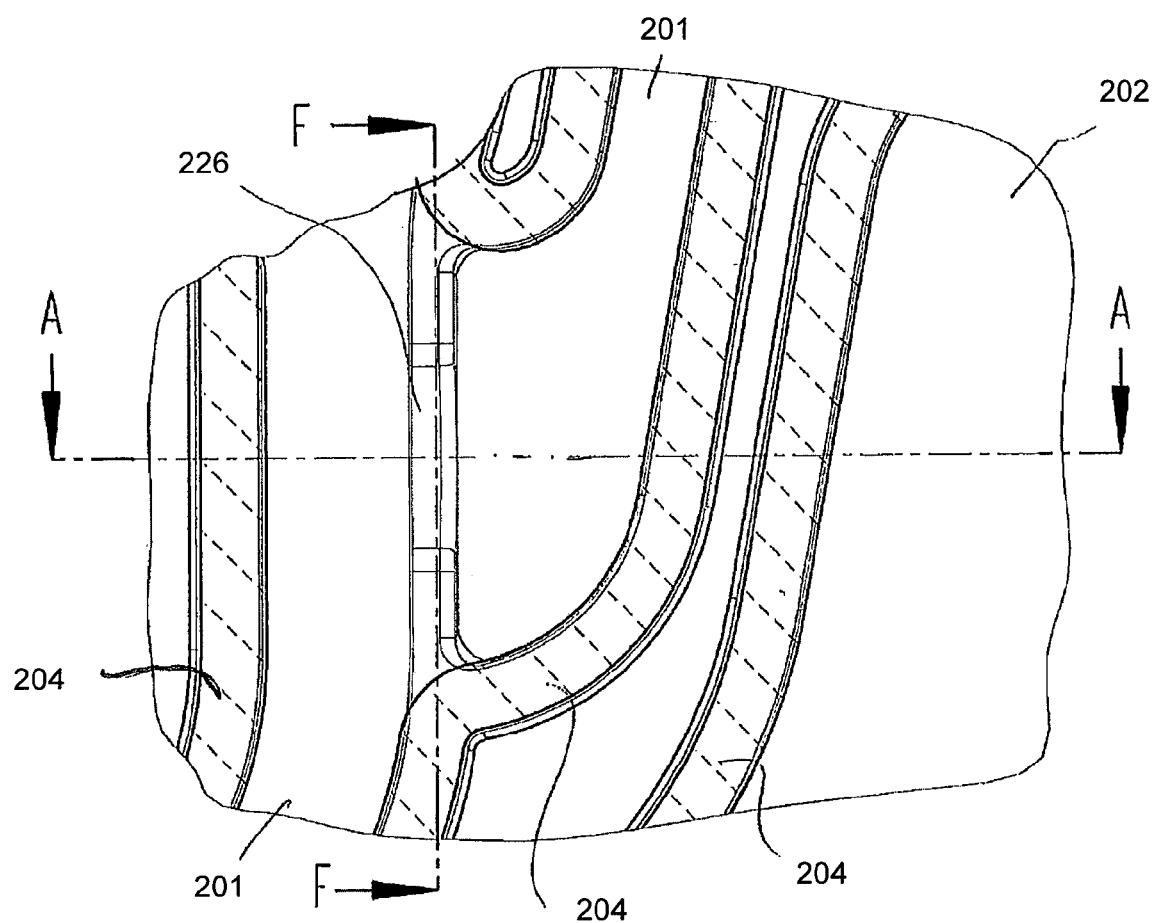
FIG. 4 shows in a top view a section of a hard part of a cassette according to the present invention.

FIG. 4 shows, in a top view, a section of a hard part 1 of a cassette 1000, for example the one of the aforementioned figures. The hard part has channels 201, a chamber 202, closed, flat channel edge bars 204 at which the film 3 is glued to or welded on the hard part 1. Furthermore, a section 226 of the hard part 1, realized as dented, is illustrated which continues into the channel edge bar 204 or interrupts it. The film 3 is not glued to or welded on the section 226 of the hard part 1 disposed beneath it, thus enabling the valve effect mentioned above. The section 226 is herein denoted as film sealing seat-bar 226.

Figure 5:
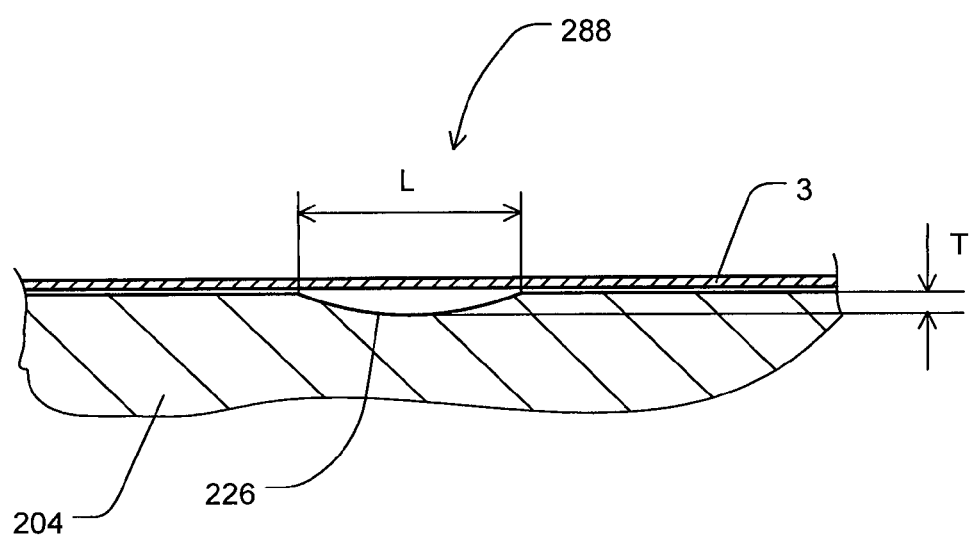
FIG. 5 shows the valve base illustrated in FIG. 4 in an enlarged view.

FIG. 5 shows the valve base 226 illustrated in FIG. 4 in an enlarged view. The valve base comprises a dent depth T, a dent width and a valve base or sealing seat bar length L. The non-illustrable dent depth extends into the drawing plane. The valve base 226 is concave in particular to the plane in which the film 3 extends. Due to its dent form or concave form, the valve base 226 is a non-straight section as defined by the present invention.

Figure 6:
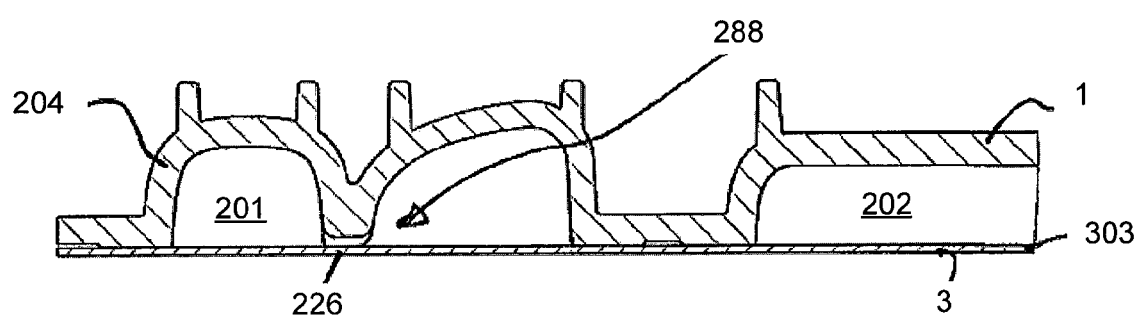
FIG. 6 shows a section through the blood treatment cassette of the FIG. 4 along the line A-A with a view towards the arrow.

FIG. 6 shows a cut through the cassette 1000 of FIG. 4 along the line A-A with a view towards the arrows.

Figure 7:
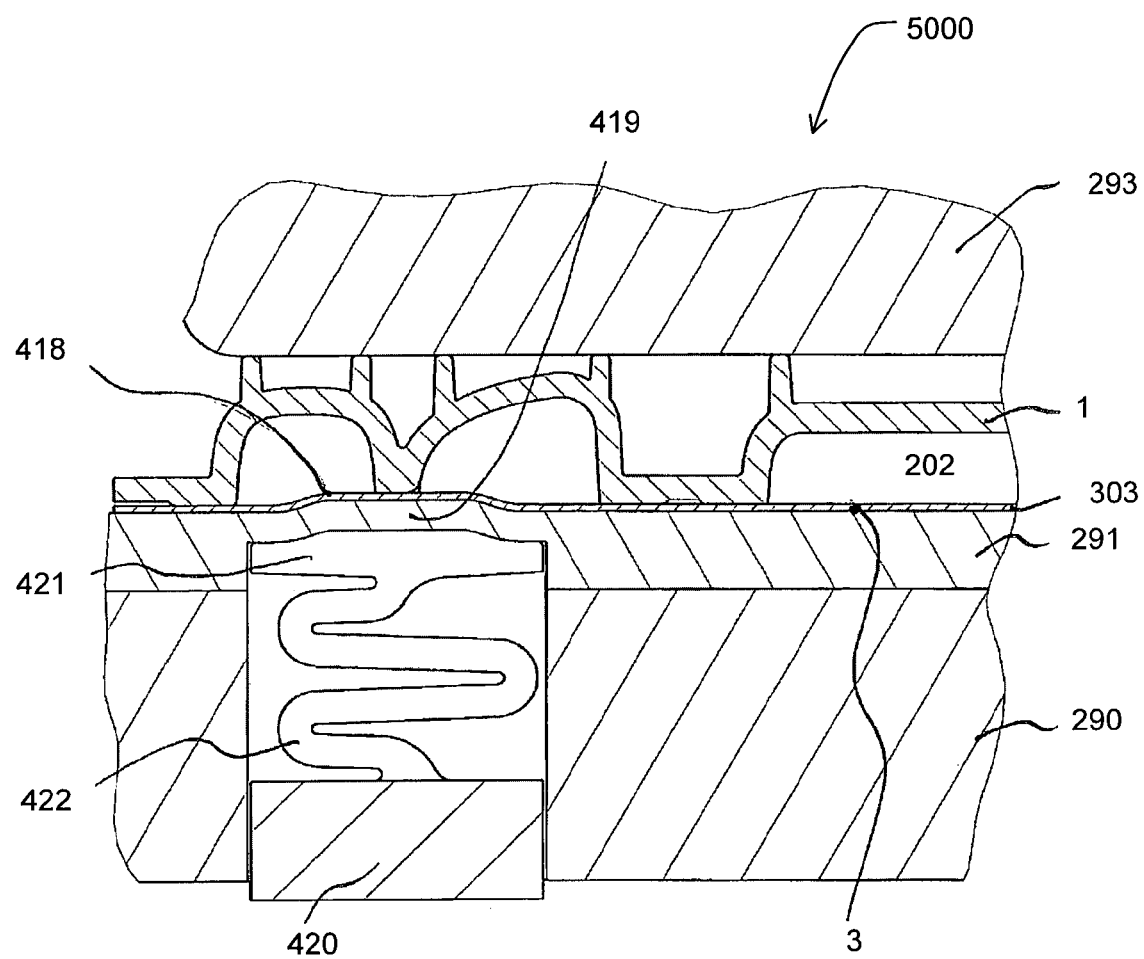
FIG. 7 shows the cassette of the FIG. 6, inserted in an embodiment of the blood treatment apparatus and pressed by the latter between the door and actuator-sensor-mat.

FIG. 7 shows the cassette 1000 of FIG. 6, inserted in an embodiment of a blood treatment apparatus 5000 and pressed by the latter between a door 293 and an actuator-sensor-mat 291. The cassette 1000 is shown herewith in an equipped and ready-to-use state, namely in sections, from the side (with reference to the sheet of FIG. 7) with a horizontally-arranged film plane or main extension plane 303 of the connection between hard part 1 and film 3.

In the exemplary embodiment of FIG. 7, an actuator 420, suitable to the film valve sealing seat, of the actuator-sensor-plate 290 extends with its front section into the section 419, which is thinner than the adjacent sections of the actuator-sensor-mat 291 or has a reduced wall thickness, of the actuator-sensor-mat 291 attached to the sealing seat. The thinner section 419 raises, when operated by means of an actuator, the actuator-sensor-mat 291 to an elevation or rising 418 which closes the valve 288 (i.e., transferring it into the second position).

The actuator provided for closing the valve 288 may exemplary be the pressure stamp or the pressing stamp shown in FIG. 7, which is in contact with the thinner section 419 of the actuator-sensor-mat 291.

The pressure stamp or pressing stamp of FIG. 7 may optionally be laminated or may comprise several sublaminated or laminated stamps which may, separated from each other, act on the film 3.

Figure 8:
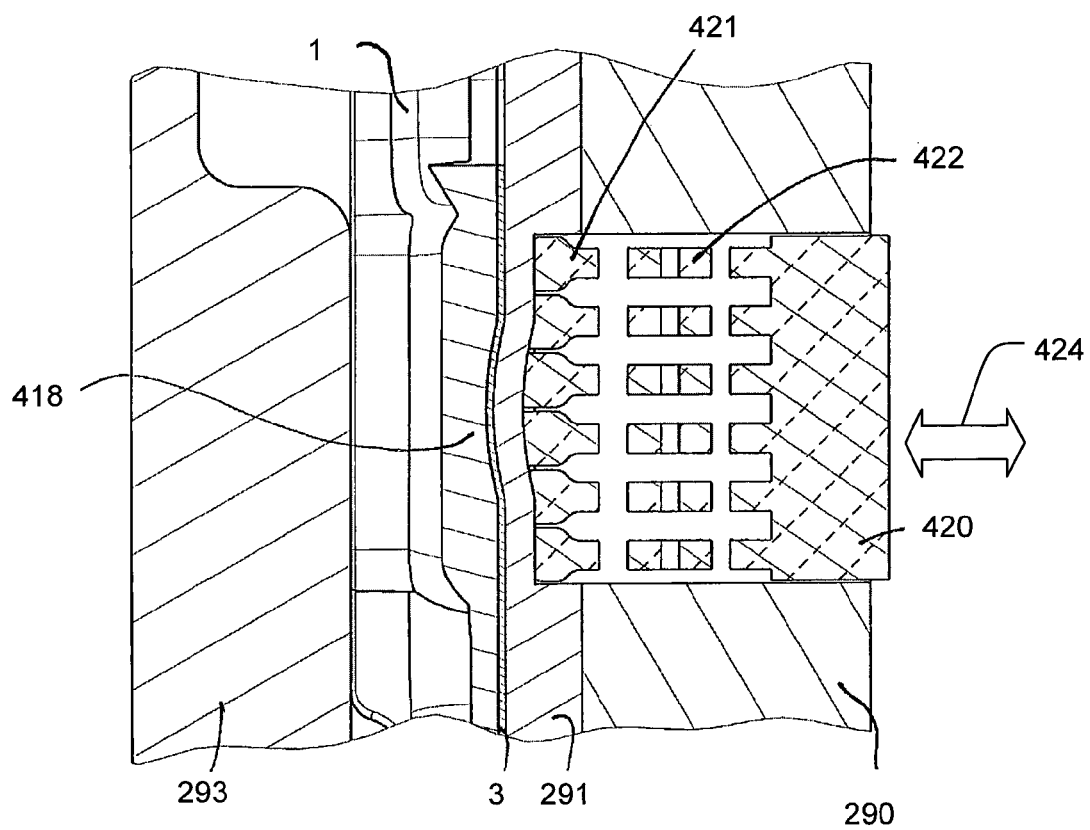
FIG. 8 shows the blood treatment cassette according to the present invention in a further embodiment inserted in an embodiment of the blood treatment apparatus and pressed by the latter between the door and actuator-sensor-mat.

Thus, the pressure stamp or pressing stamp of FIG. 8 comprises e.g., one or several laminated stamps 421, one or several laminated springs 422 and one or several relocatable or solidly built stamp bodies 420 or is made up therefrom. The illustrated pressure stamp or pressing stamp is, for example, a fiber-reinforced thermoplast. The latter may advantageously be produced at low cost.

For the tolerance balance or tolerance compensation in X-direction, which corresponds to the horizontal direction in FIG. 8, between the cassette 1000 and blood treatment apparatus 5000, an elevation or rising or buckling 418 of the actuator-sensor-mat 291 on the segmented front side of the pressure stamp or pressing stamp prismatically extends into a form adjusted to the valve base 226 in X-direction towards left and right of the valve sealing seat edge 226.

For the tolerance balance in the Y-direction which corresponds to the vertical direction in FIG. 8, a segmentation of the actuator into independent, single, springy, flexible, laminated stamps may take place.

The lamination of the pressure stamp or pressing stamp, may prevent a tolerance problem using dented film valves which results in a tolerance-related shift between cassette and blood treatment apparatus in Y-direction to a clearly geometrical maladaptation or mismatch in Z-direction between the valve sealing seat dent 226 in the hard part 1 and the pre-formed buckling in the actuator-sensor-mat 291. This may implicate that along the sealing seat edge 226, on the one hand and with regard to the middle of the valve, unpressed cavities may arise, and on the other hand higher pressed areas may arise, respectively, which lets the preformed buckling of the actuator-sensor-mat 291 deviate from its optimal form. Thereby, an evenly-pressed and complete adaptation of the film at the dented valve sealing seat edge 226 may be canceled and the valve 288 may become leaky. This may advantageously be prevented by means of the lamination described herein (to be understood also as segmentation).

Due to the lamination or segmentation, the individual laminated stamps, which under almost constant pressure force (depending on the spring characteristic of the laminated spring) may extend or compress in Z-direction where they individually adapt to the dent of the cassette 1000 moved in Y-direction and where they, sufficiently precise, adopt the shape and place of the elevation or rising. In this way, valve sealing is achieved also under the influence of fluctuating entire pressure forces and by local wears and relaxations of the actuator-sensor-mat 291.

Here, the exemplarily represented one-piece design of the laminated pressure stamp or pressing stamp is particularly advantageous because no sliding arrangement of individual segments is present here, which because of the associated slip-stick effects may thwart a continuous and strength-constant shift of the segments or the lamellae, rather, a sliding, friction-free arrangement of the solid joints is achieved.

Likewise, exemplarily and particularly favorable is a mobile arrangement along the double arrow 424 of the pressure stamp or pressing stamp in Z-direction relative to the actuator sensor plate 290. In this way for example, a spring or a compressed air actuator may load the entire stamp with a constant force which corresponds to the necessary total compression force for the closing position of the valve 288 and which is a further element of the tolerance, relaxation and wear balance. Since it is possible to switch off this force or limit the possible path according to the type of arrangement of the spring and mode of operation of a stamp actuator depending on the equipping position of the cassette 1000, a protection of the material of the actuator-sensor-mat 291 for the operating conditions with unequipped cassette 1000 is reached at the same time.

A similar effect like the exemplarily represented lamella springs on bending-joint basis may unfold pressure stamps or pressing stamps; those which are segmented similar to the represented stamp and contain springy elements for example a flexible layer made of preferably closed-cell foam. In some exemplary embodiments according to the present invention, the lamellae may even be omitted, whereby the foam is arranged directly between actuator-sensor-mat 291 and pressure stamp or pressing stamp. The mobile pressure stamp serves for the production of the defined global valve pressure force and the tolerance balance or tolerance compensation described last.

A similar effect may unfold, instead of the foam, a fluid-close cushion made of elastomer material with gas filling or gel filling, inserted between actuator-sensor-mat 291 and the pressure stamp or pressing stamp. A further solution possibility similar to the above-described lamellae pressure stamp or pressing stamp may also unfold, for example, an extruded profile made of elastomer which comprises, on the front area, ribs similar to the aforementioned lamellae and which comprises in the interior, parallel to the ribs, and, for example, centrically beneath each rib, continuous hollow sections. If one provides short distributed pieces of ribs or single humps, e.g., quadratic humps instead of ribs, one obtains then a tolerance-balancing or tolerance-compensating pressure stamp or pressing stamp whose tolerance-balancing or tolerance-compensation effect unfolds not only in one spatial direction like the above-mentioned spatial direction along the sealing seat edge 226, but in both spatial directions. This may be advantageous for film valves 288 with both long and wide sealing seat areas 226, as they may exemplary occur when connecting chambers 202 and channels 201 which are distant from each other.

Figure 9:
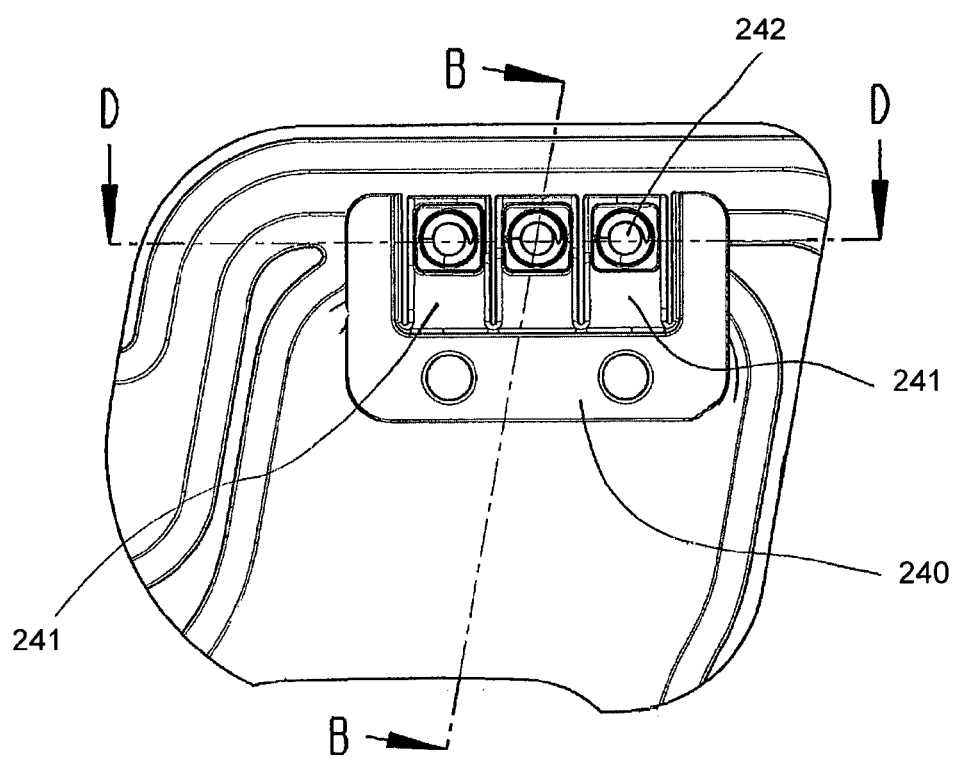
FIG. 9 shows in a top view an embodiment of a blood treatment cassette inserted in a blood treatment apparatus and pressed by the latter according to the present invention.
Figure 10:
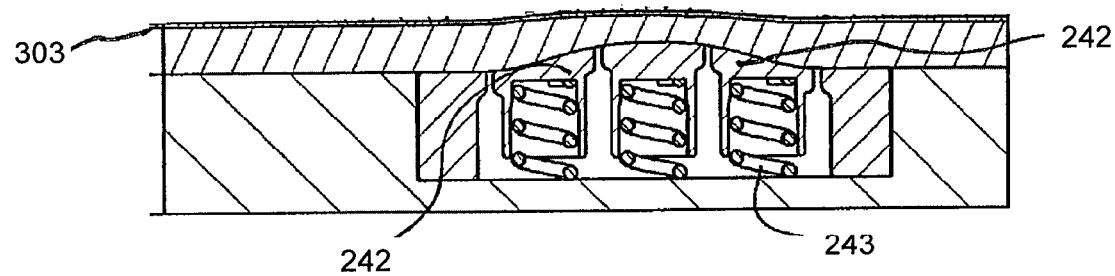
FIG. 10 shows in a sectional view along the line D-D of FIG. 9, an embodiment of a blood treatment cassette inserted in a blood treatment apparatus and pressed by the latter according to the present invention.

FIG. 9 to FIG. 10 show an embodiment of a cassette 1000 inserted in the blood treatment apparatus 5000 and pressed by the latter, i.e., in an equipped state, in a top view (FIG. 9) and in part-sectional view along the line D-D of FIG. 9 (in FIG. 10) with a horizontally arranged film plane.

In FIG. 9 one can see from the blood treatment apparatus 5000 only a pressure stamp or pressing stamp 240 as part of an actuator-sensor-plate 290. The pressure stamp or pressing stamp 240 is an example of an actuator. In this exemplary embodiment according to the present invention, the pressure stamp or pressing stamp 240 is divided into laminated stamp 242 (part-actuators), see FIG. 10, which are attached to the base body or core of the pressure stamp or pressing stamp 240 by the bending joints 241.

Thereby an assembling tolerance balance or tolerance compensation results between cassette 1000 and blood treatment apparatus 5000. Further, the valve sealing press force spreads durably and evenly on the entire valve base during use. For generating a relaxation-free force, exemplary spiral springs 243 made of spring steel are provided which are easily inserted and adjusted in a pocket or slot of the actuator-sensor-plate 290 during the assembling of the pressure stamp or pressing stamp. The complete pressure stamp 240 may be produced with low cost from unreinforced or fiber-reinforced thermoplastics in open/close injection molding.

The invention claimed is:

1. A blood treatment cassette comprising:

a cassette body comprising a hard part and a film, wherein the film is connected to the hard part and at least partially covers the hard part such that an outer surface of the film forms an exterior of the cassette, wherein the hard part comprises channel edge bars to which the film is attached such that channels that are separated by the channel edge bars are defined within the cassette, and wherein the hard part comprises at least one valve base of a valve, the valve base comprising a channel edge bar with a recessed concave area extending from one portion of the channel edge bars to another portion of the channel edge bars, wherein the channel edge bar of the valve base comprises a wall separating a first channel from a second channel, wherein the valve is configured to take: (i) a first, open position in which the valve base and a section of the film arranged above the valve base do not touch each other such that a fluid path between the first and second channels via the valve is open, and (ii) a second, closed position when applying force on the section of the film, in which the valve base and an interior surface of the section of the film touch each other such that the fluid path between the first and second channels via the valve is closed.

2. The blood treatment cassette according to claim 1, wherein the valve is configured to be transferrable from the first position into the second position by pressure applied on the valve by an actuator of a blood treatment apparatus connected to the blood treatment cassette for performance.

3. The blood treatment cassette according to claim 2, wherein the valve is a film or phantom valve.

4. The blood treatment cassette according to claim 1, wherein the valve is a film or phantom valve.

5. The blood treatment cassette according to claim 1, wherein a dent depth (T) of the valve base is 1 to 3 times the thickness of the film or wherein the valve base is reset behind adjacent channel edge bars to 1 to 3 times the thickness of the film, towards the interior of the cassette.

6. A blood treatment apparatus according to claim 5, wherein the dent depth (T) is increasing or decreasing.

7. A blood treatment apparatus connected or provided, configured or suitable to be connected with the blood treatment cassette according to claim 1, and further comprising an actuator-sensor-plate, wherein the actuator-sensor-plate comprises at least one actuator having at least two part-actuators that are separated from each other and arranged to individually extend and apply force, independently of one another, on the section of the film to individually adapt the section of the film into contact with the concave section of the valve base.

8. The blood treatment apparatus according to claim 7, wherein the actuator-sensor-plate comprises an actuator-sensor-mat facing the blood treatment cassette, wherein said actuator-sensor-mat comprises a section which is thinner than its adjacent sections and which faces the valve base of the blood treatment cassette.

* * * * *

UNITED STATES PATENT AND TRADEMARK OFFICE
CERTIFICATE OF CORRECTION

PATENT NO. : 10,596,308 B2
APPLICATION NO. : 15/126261
DATED : March 24, 2020
INVENTOR(S) : Martin Lauer It is certified that error appears in the above-identified patent and that said Letters Patent is hereby corrected as shown below:

In the Claims

Claim 6
Column 16, Line 13, delete "blood treatment apparatus" and insert --blood treatment cassette--.

Signed and Sealed this
Twenty-sixth Day of May, 2020

Andrei Iancu
*Director of the United States Patent and Trademark Office*